United States Patent
Lopatin et al.

(10) Patent No.: US 7,934,414 B2
(45) Date of Patent: May 3, 2011

(54) METHOD AND APPARATUS FOR MANUFACTURING A MEASURING DEVICE FOR DETERMINING AND/OR MONITORING A PROCESS VARIABLE AND MEASURING DEVICE

(75) Inventors: Sergej Lopatin, Lörrach (DE); Burkhard Lutterbeck, Steinen (DE)

(73) Assignee: Endress + Hauser GmbH + Co. KG, Maulburg (DE)

( * ) Notice: Subject to any disclaimer, the term of this patent is extended or adjusted under 35 U.S.C. 154(b) by 343 days.

(21) Appl. No.: 10/583,096

(22) PCT Filed: Dec. 14, 2004

(86) PCT No.: PCT/EP2004/053458
§ 371 (c)(1),
(2), (4) Date: May 18, 2007

(87) PCT Pub. No.: WO2005/059475
PCT Pub. Date: Jun. 30, 2005

(65) Prior Publication Data
US 2007/0227243 A1 Oct. 4, 2007

(30) Foreign Application Priority Data

Dec. 18, 2003 (DE) .................................. 103 59 869
Jan. 22, 2004 (DE) .......................... 10 2004 003 460

(51) Int. Cl.
*G01D 18/00* (2006.01)
*G01B 17/00* (2006.01)
(52) U.S. Cl. ............................ 73/1.82; 73/1.01; 73/1.83
(58) Field of Classification Search .................... 73/1.01, 73/1.02, 1.73, 1.182, 1.83
See application file for complete search history.

(56) References Cited

U.S. PATENT DOCUMENTS

| | | | |
|---|---|---|---|
| 2,520,520 A * | 8/1950 | Woodard | 116/27 |
| 3,760,482 A * | 9/1973 | Kawamura | 29/896.22 |
| 4,004,166 A * | 1/1977 | Nakata | 310/312 |
| 4,594,584 A * | 6/1986 | Pfeiffer et al. | 340/620 |
| 4,620,446 A * | 11/1986 | Jensen et al. | 73/652 |
| 4,920,787 A * | 5/1990 | Dual et al. | 73/54.41 |

(Continued)

FOREIGN PATENT DOCUMENTS

DE 196 51 362 C1 6/1998

(Continued)

OTHER PUBLICATIONS

"Level Limit Switch Liquiphant FTL 360/FTL 361", Endress+Hauser, 2000.*

*Primary Examiner* — David A. Rogers
(74) *Attorney, Agent, or Firm* — Bacon & Thomas, PLLC

(57) ABSTRACT

A method for manufacturing a measuring device for determining and/or monitoring a process variable of a medium in a container. The measuring device includes: A mechanically oscillatable unit, which is securable via a securement to a sensor housing and/or to the container; and a driver/receiver unit, which excites the mechanically oscillatable unit to oscillate, or receives the oscillations of the mechanically oscillatable unit. The mechanically oscillatable unit is excited to oscillate, and the reaction forces and/or reaction moments are detected, which act on the securement due to the oscillations of the mechanically oscillatable unit, that a report is issued, when the reaction forces and/or reaction moments exceed predeterminable limit values, and that, in the case of a report, the mechanically oscillatable unit is adjusted as regards its oscillation properties.

10 Claims, 4 Drawing Sheets

U.S. PATENT DOCUMENTS

| | | | | |
|---|---|---|---|---|
| 5,440,455 | A | * | 8/1995 | Rottmar ........................ 361/809 |
| 5,709,558 | A | * | 1/1998 | Dreyer et al. .................... 439/95 |
| 6,051,783 | A | * | 4/2000 | Dreyer et al. ................. 174/522 |
| 6,205,855 | B1 | | 3/2001 | Pfeiffer |
| 6,236,322 | B1 | * | 5/2001 | Lopatin et al. ................ 340/612 |
| 6,389,891 | B1 | * | 5/2002 | D'Angelico et al. ....... 73/290 V |
| 6,484,109 | B1 | | 11/2002 | Lofall |
| 6,644,116 | B2 | * | 11/2003 | Getman et al. ............. 73/290 V |
| 6,647,786 | B2 | * | 11/2003 | Ohta et al. ................. 73/504.16 |
| 6,698,287 | B2 | * | 3/2004 | Kubena et al. ............. 73/504.12 |
| 7,334,452 | B2 | * | 2/2008 | Matsiev et al. .............. 73/24.06 |
| 2003/0056590 | A1 | * | 3/2003 | Yanagisawa et al. ...... 73/504.16 |
| 2004/0118206 | A1 | * | 6/2004 | Ohta et al. ................. 73/504.16 |
| 2006/0095223 | A1 | * | 5/2006 | Gordon et al. ................ 702/116 |

FOREIGN PATENT DOCUMENTS

| | | |
|---|---|---|
| DE | 197 28 653 A1 | 1/1999 |
| DE | 103 18 445 A1 | 11/2004 |
| EP | 0 949 489 A1 | 10/1999 |
| JP | 04369447 A * | 12/1992 |
| WO | WO 94/14047 | 6/1994 |
| WO | WO 2004/094964 A1 | 11/2004 |

* cited by examiner

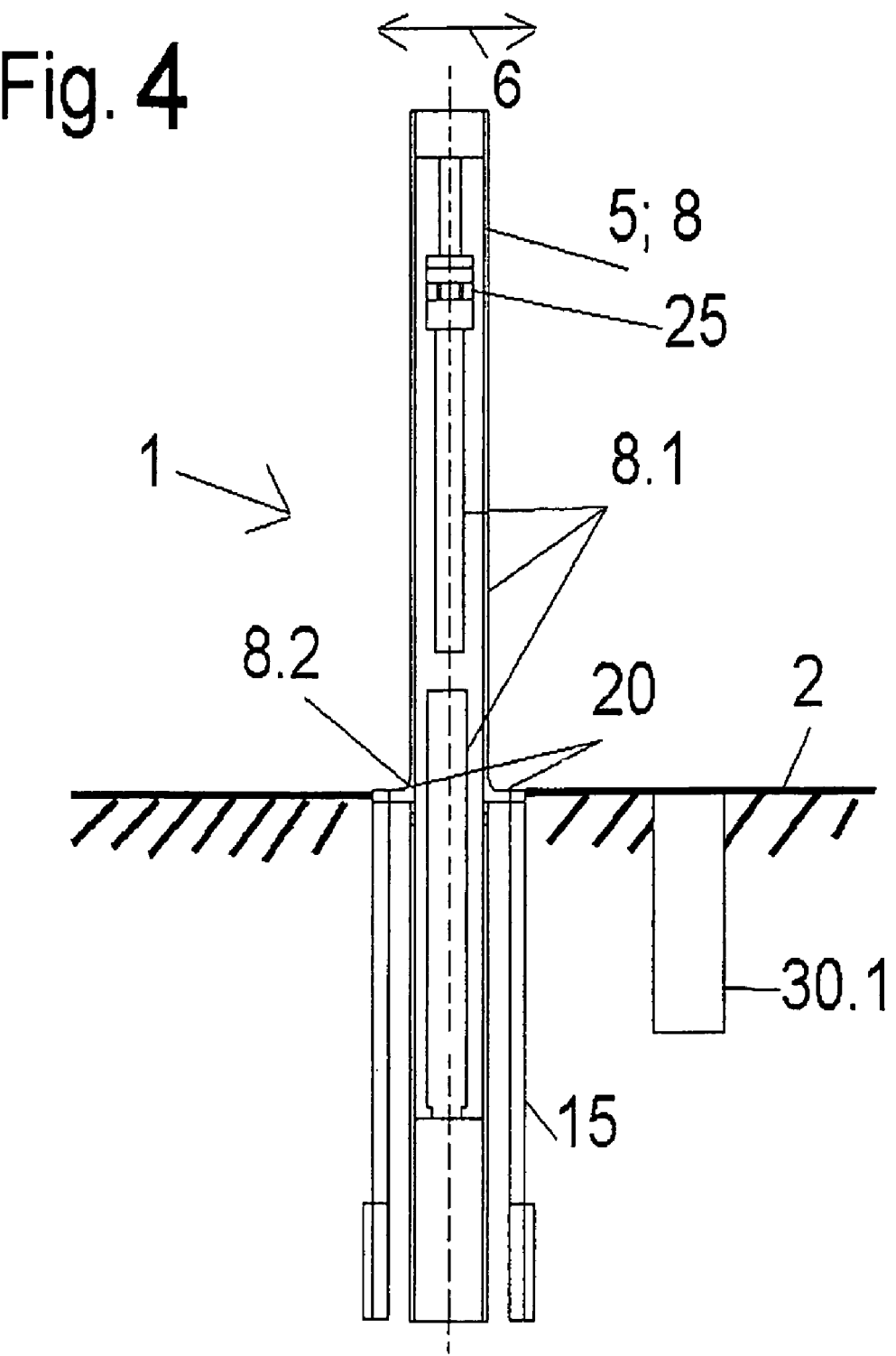

METHOD AND APPARATUS FOR MANUFACTURING A MEASURING DEVICE FOR DETERMINING AND/OR MONITORING A PROCESS VARIABLE AND MEASURING DEVICE

FIELD OF THE INVENTION

The invention relates to a method for manufacturing a measuring device for determining and/or monitoring a process variable of a medium in a container. Additionally, the invention relates to an apparatus for manufacturing such a measuring device, and the invention relates to a measuring device itself. The process variable can be, for example, fill level, density or viscosity of the medium in the container. The mechanically oscillatable unit can be, for example, an oscillatory fork, or a single-rod.

BACKGROUND OF THE INVENTION

The measuring device includes: A mechanically oscillatable unit, which can be secured via a securement to a sensor housing and/or to the container; and a driver/receiver unit, which excites the mechanically oscillatable unit to oscillate, or receives oscillations of the mechanically oscillatable unit, as the case may be.

Endress + Hauser manufactures and sells fill level measuring devices under the mark LIQUIPHANT. These measuring devices include, as the mechanically oscillatable unit, an oscillatory fork of two tines, which are excited to mechanical oscillations via a membrane, or diaphragm, by a piezoelectric element as driver/receiver unit. In such case, the two tines of the fork oscillate with opposite phase relative to one another. If the medium, whose fill level is to be monitored, comes in contact with the oscillatable unit, then this leads to a change in the frequency and/or amplitude of the oscillations. In this way, the reaching of a fill level can be detected. Correspondingly, it is also possible to detect the subceeding, or falling beneath, of a fill level, i.e. when the oscillating fork is initially covered by medium and then the level sinks. The membrane, on which the oscillatable unit is attached and via which it is excited to oscillate, or via which the oscillations are received, as the case may be, is connected with a housing of the device, or with a container wall, via a securement. Additionally usually provided in the measuring device is an amplifying unit, which amplifies and feeds-back the received signals.

Important in the case of oscillatory forks, but also in the case of all other mechanically oscillatable units used in field, or measuring, devices, is the symmetry of the oscillatable unit. Thus, it must be assured in the oscillating fork that both tines oscillate in opposite phase in such a manner that reaction forces, and moments acting on the securement are minimized as much as possible. To this end, it is e.g. required that both tines have equal mass moments of inertia, thus also equal torques. The oscillatable unit is thus symmetrically constructed, when its oscillations do not lead to reaction forces, and moments, on the securement, thus, when there are components of the mechanically oscillatable unit—e.g. the mentioned tines of the fork—whose oscillations are matched to one another, such that the forces and torques on the securement exactly cancel one another, so that the residual reaction forces, and moments, are balanced as much as possible. If an asymmetry exists—thus, if, for example, one tine is heavier than the other—then it is no longer possible to assure that the forces and moments acting on the securement compensate one another. Such compensation is, among other reasons, important for preventing loss of energy through the securement. Energy loss leads to reduction of oscillation amplitude. Additionally, an asymmetry can lead to jumping of the oscillation frequency unexpectedly between two values, a situation which can corrupt the measurement.

A method in the state-of-the-art for measuring symmetry of an oscillatory fork involves determining the oscillation frequency of each tine separately. If there are differences present, greater than a predetermined tolerance range, then e.g. the weight or the stiffness of the tines is adjusted, e.g. reduced. This measuring of the frequencies is very complicated. It occurs in the context of manufacture of the field devices. In the field, it is, above all, scarcely possible to determine the oscillation frequencies of the individual tines.

SUMMARY OF THE INVENTION

Consequently, an object of the invention is the recognition of asymmetries in mechanically oscillatable units of measuring devices.

The invention achieves this object by way of a method and apparatus for manufacture of a measuring device to make the oscillatable unit of the measuring device symmetrical. Additionally, the invention achieves the object by way of a measuring device itself, whereby it becomes possible to monitor the symmetry also during use of the measuring device, thus after installation. By the invention, it is, on the one hand, possible to prevent an asymmetry during manufacture of a measuring device and, on the other hand, it is possible, during use, to monitor symmetry and, in connection therewith, measurement accuracy.

The invention achieves the object with regard to a method for manufacturing a measuring device, by the following measures: Reaction forces and/or reaction moments are detected, which act on the securement due to the oscillations of the mechanically oscillatable unit on the securement; a report is issued, when the reaction forces and/or reaction moments exceed predeterminable limit values; and, in the case of a report, the mechanically oscillatable unit is adjusted as regards its properties affecting oscillation. An idea of the invention is, thus, that the forces and moments, which result from asymmetries, are used for assuring that these "imbalances" of the oscillatable unit—the "mismatch"—are balanced during fabrication. Due to manufacturing tolerances, it is always possible that mechanically oscillatable units are not always optimally balanced. If this "mismatch" lies above a certain and predeterminable range, then the frequencies, for example, differ by more than a predeterminable percentage from one another, and then the measurements are no longer exact and reliable, or they can even be impossible, as the case may be. Therefore, symmetry is controlled, by detecting arising forces and moments resulting from an asymmetry. If these forces and/or moments lie above certain values, then corresponding differences are present in the components of the oscillatable unit, e.g. the tines in the case of the fork, or the individual oscillating members in the case of a single-rod. These are then balanced, by an adjusting of the oscillatable unit. For instance, one tine is increased in weight, or its stiffness is changed, etc. The limit values are to be set such that no measurement errors arise, while nevertheless staying within the framework of a usual manufacturing method.

The invention achieves the object with regard to an apparatus for manufacturing a measuring device by the features that a means for securing the measuring device is provided and that at least one force detection unit is provided, which is coupled with the securement in such a manner that it detects reaction forces and/or reaction moments, which act on the securement due to oscillations of the mechanically oscillatable unit. The mechanically oscillatable unit is thus secured into a suitable apparatus. In this way, for example, no effects of an unfavorable positioning of the measuring device arise. Additionally, this also permits control of the influence of interfering vibrations. Subsequently, the force detection unit measures forces and/or moments resulting from an asymmetry. An appropriate evaluation unit for evaluating the detected forces and moments of the force detection unit is within the skill of the art.

An advantageous embodiment includes that at least one force transmission unit is provided, which is coupled with the securement and/or with the sensor housing and with the force detection unit in such a manner that the force detection unit detects via the force transmission unit reaction forces and/or reaction moments acting on the securement. Thus, in this embodiment, the reaction forces and moments, which result from the oscillation asymmetry, are transmitted via a force transmission unit, so that e.g. the force detection unit can be located farther removed from the mechanically oscillatable unit. This is e.g. advantageous in the manufacture of the measuring devices, or of the mechanically oscillatable units, since, in this way, the symmetry can also be reviewed when the oscillatable unit has lesser dimensions, thus when insufficient space is present, in order to connect the force detection unit directly with the oscillatable unit. Furthermore, the force transmission unit serves in the case of application of the invention in the case of manufacturing/output control of the mechanically oscillatable unit, or of the measuring devices, also for the securing of the measuring device in the measuring of symmetry.

An embodiment of the apparatus provides that the force transmission unit involves a flange. Such a flange is most often also heavy enough relative to the measuring device, so that the device is safely and tightly secured by clamping.

The invention achieves the object as regards a measuring device by the features that at least one force detection unit is provided, which is coupled with the securement in such a manner that it detects reaction forces and/or reaction moments, which act on the securement due oscillations of the mechanically oscillatable unit. An idea is thus to make use of the fact that asymmetries result in forces and moments being transmitted outwards from the oscillatable unit onto the securement. In the invention, thus, the results of the asymmetry are used for its detection. In such case, the force detection unit is, here, in contrast with the above method and above apparatus, which relate also to measuring devices lacking continuous monitoring of symmetry, a permanent component of the measuring device, in order to determine or monitor the symmetry of the mechanically oscillatable unit also during use of the measuring device in the field. In use of the measuring device, this force detection unit serves also for predictive maintenance. Because symmetry is monitored during operation, following installation, it is permanently assured that the quality of the measurements does not degrade due to a decreased symmetry. In the case of advanced diagnostics, the evaluation of the time behavior of the symmetry thus enables determination in advance, whether, and when, a replacement—in the case of corrosion or abrasion as cause of the lessened symmetry—or a cleaning—in the case of accretion—is due for the oscillatable unit. For determining symmetry, also tolerances are to be specified. This relates to the fabrication, but also to application in the field. A problem is that also forces and moments result from oscillations in the environment, for instance, because a stirrer is leading to vibrations of the container wall. The forces and moments from these movements must be kept out of the reaction forces and moments, e.g. by a frequency analysis or by comparison with the oscillations of the oscillatable unit.

An embodiment provides that the force detection unit is arranged in such a manner that it detects reaction forces and/or reaction moments along an axis which essentially coincides with the oscillation axis of the mechanically oscillatable unit. By this arrangement, a very great sensitivity results, whereby the symmetry can be determined more accurately and better. The reason for this is that, in the case of deviations from symmetry, the energy is preferentially transmitted in the direction of the oscillatory axis onto the clamping mechanism. In general, the force detection unit should be arranged relative to the mechanically oscillatable unit in such a manner that sensitivity is as high as possible.

An embodiment includes that the force detection unit is an acceleration sensor. In such case, a sensor of the highest possible sensitivity should be used.

An embodiment provides that the mechanically oscillatable unit is an oscillatory fork. Corresponding devices are manufactured by the assignee under the marks LIQUIPHANT and SOLIPHANT.

An embodiment provides that the mechanically oscillatable unit is a single-rod. Single-rods have, for example, the advantage that, in this way, contact with the medium is lessened. Also, single-rods avoid a problem with forks, that material can get stuck between the tines.

A further embodiment includes that the mechanically oscillatable unit is a single-rod containing three oscillatory members, and that at least one oscillatory member is connected in a connection region with the securement. See, in this connection, German patent application No. 103 31 730.9 of the assignee. Such single-rods can experience difficulties in application concerning accretions, which are usually asymmetrical, and concerning corrosion, which likewise most often occurs asymmetrically. In application of the measuring devices, it is thus possible to find, in the case of single-rods, that the symmetry of the mechanically oscillatable unit has been compromised by the process, or by the medium, as the case may be.

BRIEF DESCRIPTION OF THE DRAWINGS

The invention will now be explained in greater detail on the basis of the appended drawings, the figures of which show as follows:

FIG. 4 a schematic drawing of use of a measuring device of the invention of a second type—here a single-rod, in contrast to the oscillatory fork in FIGS. 1 to 3.

DESCRIPTION OF THE PREFERRED EMBODIMENTS

Figure 1:
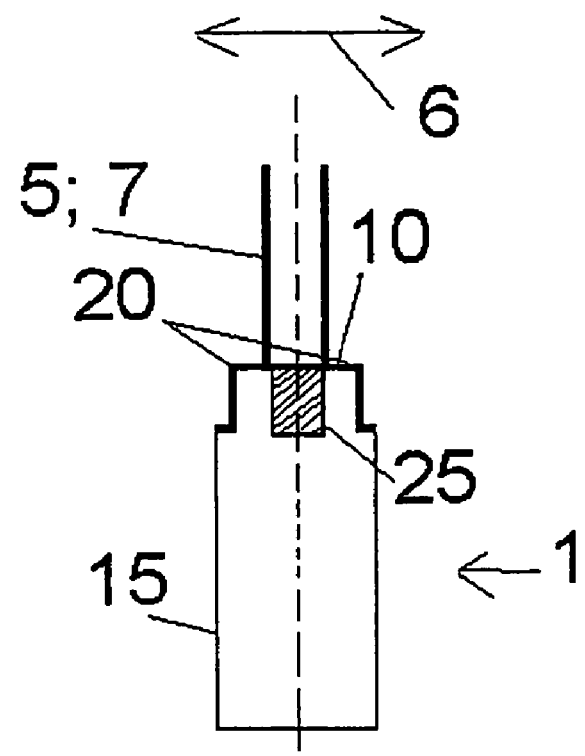
FIG. 1 a schematic drawing of an oscillatory fork as measuring device according to the state of the art.

FIG. 1 shows the measuring device 1. It is composed of a sensor housing 15, in which is located the driver/receiver unit 25—e.g. a piezoelectric unit. This driver/receiver unit 25 excites, via a membrane 10 secured to the housing 15 via the securement 20, the mechanically oscillatable unit 5 to oscillate. As the case may be, the driver/receiver unit 25 also detects, via the membrane 10, oscillations of the mechanically oscillatable unit 5. Unit 5 is, in this case, an oscillatory fork 7, the two tines of which oscillate along the oscillation axis 6 in opposite phase to one another. If both tines have equal moments of inertia, or if they are generally symmetrical to one another, then the separate forces and moments arising from the oscillations on the housing 15 at the securement 20 of the membrane 10 compensate one another. If the tines differ—if the mechanically oscillatable unit 5 is thus asymmetrical—, then residual reaction forces and moments arise at the securement 20. As a result of this, oscillatory energy can be lost, this expressing itself in a lessened sensitivity of the measuring device 1. The loss of oscillatory energy depends, among other things, on how rigidly the measuring device is secured to the housing 15 and on whether container parts (not shown) resonate. A more serious problem than the energy loss is represented by the case where the oscillation frequency jumps unexpectedly back and forth between two values, because of an asymmetry. In such case, only one tine oscillates, and the other rests. This can occur, for example, when an oscillatory fork has an asymmetry greater than 4-5% in the frequencies of the two tines, and the measuring device is secured in a massive flange.

Figure 2:
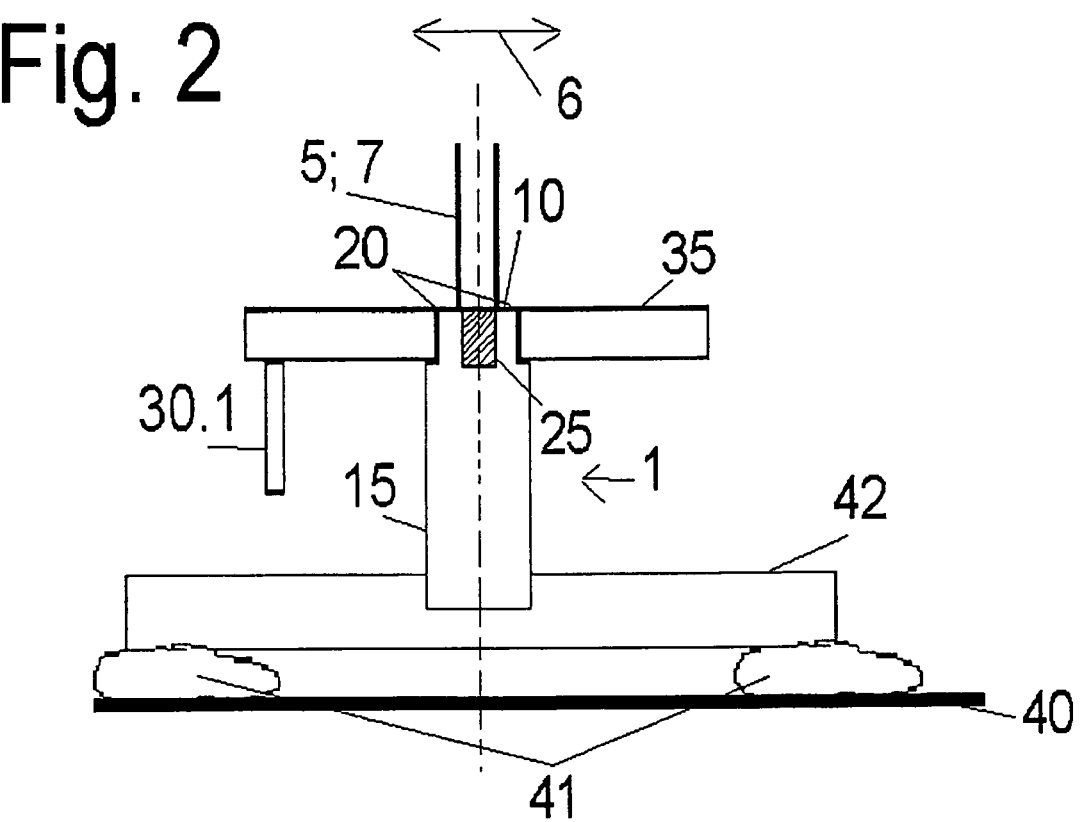
FIG. 2 a section through an apparatus of the invention for manufacturing a measuring device.

FIG. 2 shows the housing 15 secured, by clamping under the weight of the force transmission unit 35, between a support 42 and the force transmission unit 35, which is, for example, a flange. The measuring device 1 must be held securely and as stably as possible, so that only the reaction forces and moments resulting from an asymmetry of the mechanically oscillatable unit 5 are measured, and no forces, which stem e.g. from an instable positioning of the measuring device 1. For this purpose, the support 42 also rests by way of damping pads 41 on a subsurface 40. In this way, in turn, no external forces can act during the symmetry measurement. The oscillatory fork 7 oscillates, in the example shown here, in the direction of the oscillation axis 6. If the two tines are not symmetric to one another, then reaction forces and moments are transferred to the securement 20 and via the force transmission unit 35 onto the force detection unit 30.1. The force detection unit 30.1 is, for example, an acceleration sensor. The example illustrated in this FIG. 2 thus relates to the fabrication of the measuring device 1, wherein the symmetry can be simply and safely checked.

Figure 3:
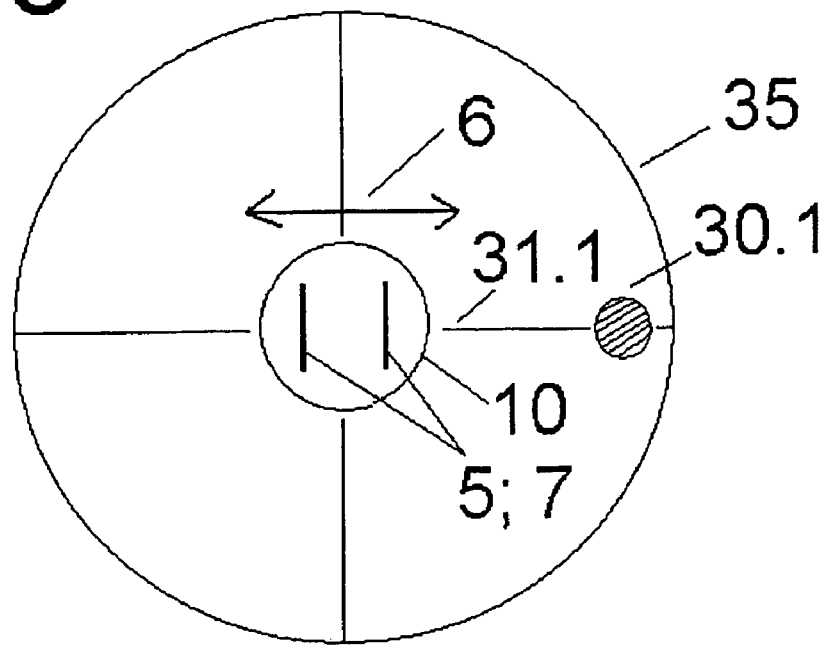
FIG. 3 a view from above onto the embodiment of FIG. 2.

FIG. 3 shows a top view of the construction in FIG. 2. Illustrated are the force transmission unit 35, with the membrane 10 and the mechanically oscillatable unit 5 in the middle. The oscillatory fork 7 oscillates along the axis 6. Also lying in this direction is the detection axis 31.1 of the force detection unit 30.1, which thus has the optimal sensitivity for measurement of the symmetry. If an additional, second force detection unit (not shown) is used, then it is also possible to detect which tine is lighter and which is heavier.

FIGS. 2 and 3 illustrate a case in which the invention is used during manufacture of the measuring device. FIG. 4 illustrates a measuring device, in which symmetry is monitored during operation. Thus, the invention includes a safety aspect assuring reliable measured values, or permitting a prediction based on the state of the measuring device.

FIG. 4 shows a single-rod 8 as the mechanically oscillatable unit 5 of a measuring device 1. This measuring device 1 can be manufactured with the method of the invention and with the apparatus of the invention, but it goes beyond these subjects in that it is also monitored for symmetry during operation. This single-rod 8 is composed of three oscillatory members 8.1, with the inner oscillatory members each oscillating with opposite phase relative to one another. Located in the connection region 8.2 is the securement 20, where, in this case, the measuring device 1 is connected with the container 2, in which the medium (not shown) to be measured or monitored is located. Thus, in this case, the invention is applied in the case of use of the measuring device 1 in the field. If an accretion is formed by the medium on the single-rod 8, or if the medium is corrosive or abrasive, then the three oscillatory members and the position of the connecting region 8.2 are no longer optimally matched to one another, and energy is transferred to the container 2. This is detected by the force detection unit 30.1. Depending on the construction of the force detection unit 30.1, already very small deviations from symmetry of the mechanically oscillatable unit can be detected. In this way, it is possible, for example, in the case of special media, to keep the sensitivity of the measuring device 1 constant and very high, by very early recognition of e.g. accretion and the sensitivity loss resulting therefrom. For this purpose, e.g. an evaluation of the chronological development of the signals of the force detection unit 30.1 can be required, in order e.g. to detect growth of an accretion or loss through abrasion or corrosion.

The invention claimed is:

1. A method for manufacturing a measuring device for determining and/or monitoring a process variable of a medium in a container, the method comprising the steps of:
   securing a mechanical oscillating unit via a securement to a sensor housing and/or to the container;
   exciting the mechanical oscillating unit to oscillate using a driver/receiver unit;
   detecting reaction forces and/or reaction moments which act on the securement due to the oscillations of the mechanical oscillating unit and which result from an asymmetry of the mechanical oscillating unit using a force detection unit mechanically coupled to the securement;
   issuing a report, when the reaction forces and/or reaction moments exceed predeterminable limit values; and
   when a report is issued, making the mechanical oscillating unit symmetric by adjusting the mechanical oscillating unit with regard to its oscillation properties.

2. An apparatus for adjusting a measuring device having a mechanical oscillating unit and a securement, the apparatus comprising:
   at least one force detection unit; and
   means for securing the measuring device to said at least one force detection unit such that the force detection unit, mechanically coupled to said securement in such a manner that it detects reaction forces and/or reaction moments, which act on said securement due to the oscillations of the mechanical oscillating unit and which result from an asymmetry of the mechanical oscillating unit.

3. The apparatus as claimed in claim 2, wherein:
   said means for securing includes at least one force transmission unit, which is coupled with said securement and/or with a sensor housing and with said at least one force detection unit in such a manner that said at least one force detection unit detects, via said force transmission unit, reaction forces and/or reaction moments acting on said securement.

4. The apparatus as claimed in claim 3, wherein:
   said force transmission unit comprises a flange.

5. A measuring device for determining and/or monitoring a process variable of a medium in a container, comprising:
   a mechanical oscillating unit, which is secured via a securement to a sensor housing and/or to the container;
   a driver/receiver unit, which excites said mechanical oscillating unit to oscillate; and
   at least one force detection unit, mechanically coupled to said securement in such a manner that it detects reaction forces and/or reaction moments, which act on said securement due to the oscillations of said mechanical oscillating unit and which result from an asymmetry of the mechanical oscillating unit.

6. The measuring device as claimed in claim 5, wherein: said force detection unit is arranged in such a manner that it detects reaction forces and/or reaction moments along an axis essentially coinciding with an oscillation axis of said mechanical oscillating unit.

7. The measuring device as claimed in claim 5, wherein: said force detection unit comprises an acceleration sensor.

8. The measuring device as claimed in claim 5, wherein: said mechanical oscillating unit comprises an oscillatory fork.

9. The measuring device as claimed in claim 5, wherein: the mechanical oscillating unit comprises a single-rod.

10. A measuring device for determining and/or monitoring a process variable of a medium in a container, comprising:

a mechanical oscillating unit, which is secured via a securement to a sensor housing and/or to the container;

a driver/receiver unit, which excites said mechanical oscillating unit to oscillate; and at least one force detection unit, mechanically coupled to said securement in such a manner that it detects reaction forces and/or reaction moments, which act on said securement due to the oscillations of said mechanical oscillating unit, wherein:

said mechanical oscillating unit comprises a single-rod having three oscillatory members; and at least one oscillatory member is connected at a connecting region with said securement.

\* \* \* \* \*